United States Patent [19]

Yannas et al.

[11] 4,060,081
[45] Nov. 29, 1977

[54] MULTILAYER MEMBRANE USEFUL AS SYNTHETIC SKIN

[75] Inventors: Ioannis V. Yannas, Newton Center; John F. Burke, Belmont; Philip L. Gordon, Lexington, all of Mass.; Chor Huang, Avon Lake, Ohio

[73] Assignee: Massachusetts Institute of Technology, Cambridge, Mass.

[21] Appl. No.: 596,112

[22] Filed: July 15, 1975

[51] Int. Cl.² ............................................. A61L 15/00
[52] U.S. Cl. .............................. 128/156; 128/DIG. 8
[58] Field of Search .................. 128/155, 156, 334 R, 128/DIG. 8, 325; 3/1 R

[56] References Cited

U.S. PATENT DOCUMENTS

| | | | |
|---|---|---|---|
| 3,526,224 | 9/1970 | Potts | 128/156 |
| 3,742,955 | 7/1973 | Battista et al. | 128/334 R |
| 3,800,792 | 4/1974 | McKnight et al. | 128/156 |
| 3,810,473 | 5/1974 | Cruz et al. | 128/DIG. 8 |
| 3,875,937 | 4/1975 | Schmitt et al. | 128/156 |
| 3,896,802 | 7/1975 | Williams | 128/156 |
| 3,903,882 | 9/1975 | Augurt | 128/155 |

*Primary Examiner*—Lawrence W. Trapp
*Attorney, Agent, or Firm*—Arthur A. Smith, Jr.; Martin M. Santa; David E. Brook

[57] ABSTRACT

A multilayer membrane, which is useful as synthetic skin, is disclosed herein. A first layer is formed from a material which does not provoke an immune response and which is also insoluble and nondegradable in the presence of body fluids and/or body enzymes. Preferred materials for the first layer are crosslinked composites of collagen and a mucopolysaccharide. A second layer is formed from a nontoxic material which controls the moisture flux of the overall membrane to about 0.1 to 1 mg./cm²/hr. Suitable materials for the second layer include synthetic polymers such as silicone resins, polyacrylate or polymethacrylate esters or their copolymers, and polyurethanes.

24 Claims, 1 Drawing Figure

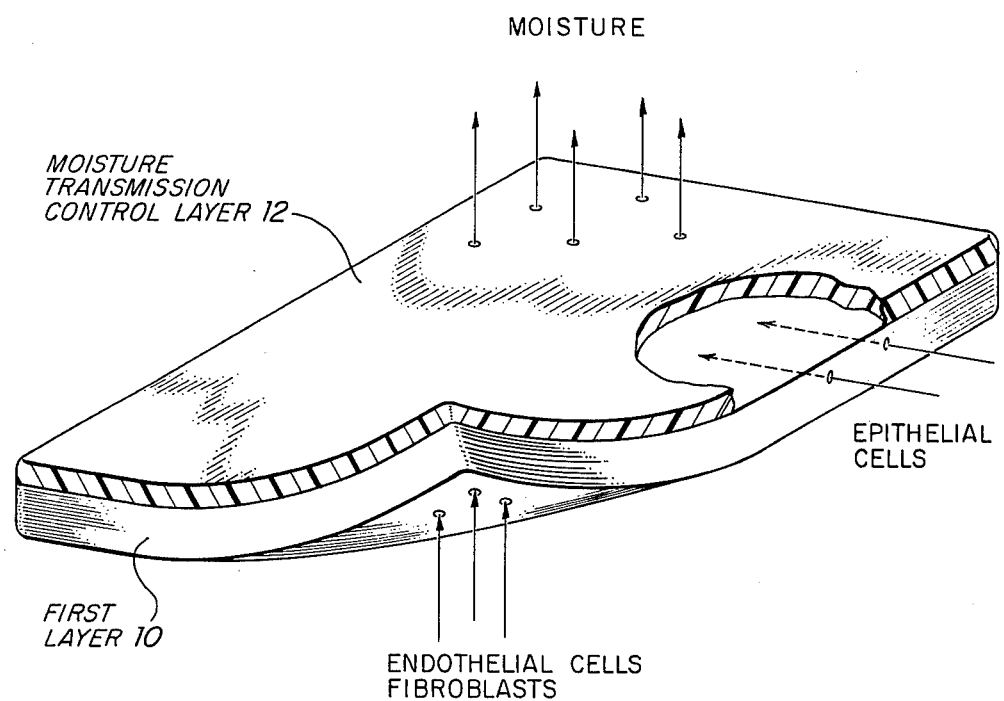

MULTILAYER MEMBRANE USEFUL AS SYNTHETIC SKIN

The invention described herein was made in the course of or under grants from the National Institute of Health.

BACKGROUND OF THE INVENTION

1. Field of the Invention

This invention is in the field of materials and more paticularly in the field of materials suitable as synthetic skin.

2. Description of the Prior Art

References to attempts to cover open wounds and severe burns go back to 1500 B.C. Breasted, J. H., *Edwin Smith, Surgical Papyrus*, vol. 1, Univ. of Chicago Press, Chicago, Illinois (1930), p. 83. Although a great deal of research effort has since been directed towards a functioning substitute for skin, no viable alternative for the autograft has yet been developed. However, the observations which have accumulated from the work already done in this area of research have resulted in the evolution of a number of basic concepts which may be applied to the design of a system for treating open wounds and third degree burns with a more realistic expectation of success.

Prior approaches which have been used to develop a skin substitute can be divided into four broad catagories, namely: homografts; modified dermal xenografts; synthetic polymeric structures; and, reconstituted collagen films.

The use of homografts in the treatment of massive burns is an accepted procedure at the present time. The source of the skin transplant may be a live donor or skin obtained from cadavers and preserved in a skin bank. The justification for the use of homografts is the necessity for reducing fluid loss, preventing infections, and reducing the area of scarring.

In the absence of immunosuppressive agents, however, homografts are almost invariably rejected. Rejection is apparently mediated primarily by the interception of graft vascularization which accompanies the onset of the immune reaction. Guthy, E. A., Billotte, J. B., Koumans, R. J. K., and Burke, J. F., in *Research in Burns*, Matter, P., Barclay, T. L. and Konickova, Z. (eds.), Hans Huber, Stuttgart, 1971. As is well known, the use of immunosuppressive agents to avoid rejection of such grafts is also accompanied by a host of problems.

Efforts to modulate the immunogenicity of homografts by organ culture techniques have been attempted by several investigators. After a number of conflicting reports, the results of a definitive investigation of such procedures was reported by Ninnemann and Good who concluded that modification of antigens in the cultured tissue had not been demonstrated in such attempts. Ninnemann, J. L. and Good, R. A., *Transplantation*, 18, 1 (1974).

An alternative approach to the use of homografts has been investigation of the possibility of modifying skin from animals. The basic goal of this approach is removal of those components in the dermis which elicit the production of host antibodies.

Oliver et al. pursued this approach by treating porcine dermis with trypsin to remove cellular and non-collagenous material. Oliver, R. F., Grant, R. A. and Kent, C. M., *Brit. J. Exp. Path.*, 53, 540 (1972). This resulted in a graft material which was primarily insoluble collagen cast in the original morphology of the dermis, with a negligible level of antigenicity. The modified dermal collagen thus obtained was grafted on to full thicknss excised skin wounds in the pig and its fate compared to that of autografts and homografts of untreated dermis. The autografts behaved in the normal manner, described previously by Henshaw and Miller. Henshaw, J. R. and Miller, E. R., *Arch. Surg.*, 658 (1965). The untreated homografts were daed by Day 5, with mononuclear cells present, and had begun to degenerate at the base by Day 10. By Day 20, the rejection of the homografts was substantially complete. With treated dermal collagen grafts, the lower part of the graft was repopulated with capillaries and fibroblasts by Day 5, while epidermal migration took place through the graft. Basophilic collagen lysis of the graft collagen started near Day 5 and was associated with infiltration of granulation tissue which progressively replaced collagen in the presence of multinuclear giant cells. By Day 20, the grafts were substantially replaced by granulation tissue and behaved like open wounds. This emphasizes the necessity for increasing the resistance of native collagen to lysis.

As a result of these experiments, Oliver et al. listed four requirements for a successful graft:

1. Dermal collagen fibers should persist unaltered for a long period, providing an essential structural framework for the reformation of the vascular and cellular elements of tissue;
2. The graft should not evoke foreign body reaction, which leads to eventual destruction of the newly cellularized graft;
3. The graft should provide a suitable dermal bed for the growth and development of normal epidermis; and,
4. The graft should suppress the formation of granulation tissue.

A third approach involves the use of synthetic polymeric structures. The literature is replete with references to the investigation of polymeric materials for a variety of biomedical applications including skin substitutes or temporary wound dressings. This is not surprising in view of the polymer scientist's capability of incorporating almost any set of physical and chemical (but, as yet, few biological) requirements into a polymeric structure. The investigations into the utility of polymeric films as skin replacements have, thus far, eliminated a considerable number of candidate materials but have resulted in useful insights into the requirements for a satisfactory skin replacement. For example, the use of a velours structure resulted in improved adhesion to tissue, and the development of methods of preparation of so-called biocompatible polymers with controlled pore size improved the possibility of synthesizing materials capable of inducing cellular migration and proliferation into the graft. See Hall, C. W., Liotta, D., Chidoni, J. J., Debakey, M. E., and Dressler, D. P., *J. Biomed. Mat. Res.*, 1, 187 (1967); and Wilkes, G. L. and Samuels, S. L., *J. Biomed. Mat. Res.*, 7, 541 (1973), respectively. Another promising approach involved polymerization of crosslinked polymers in the hydrogel form, thus providing added capability for encouraging cellular ingrowth and vascularization. Hubacek, J., Kliment, K., Dusek, J., and Hubacek, *J. Biomed Mat. Res.*, 1, 387 (1967). The use of synthetic polymers in skin replacement has not so far led to solution of the problem, however, due mainly to the high incidence of infection and the inability of the materials evaluated up to now to encourage vascularization and epithelization.

Since the major constituent of normal skin is collagen, a logical approach to the development of a skin substitute would involve study of the fate of reconstituted collagen structures when placed in contact with living tissue.

This approach was used by a number of investigators using the general procedure of extracting the collagen from animals, purifying it to various degrees and converting it to films or other structures that were used as wound dressings or implanted in living tissue to determine their in vivo fate. Earlier work in this area demonstrated that collagen per se evokes a chronic inflammatory response with subsequent resorption of the implant. Pullinger, B. D. and Pirie, A., *J. Path. Bact.*, 34, 341 (1942). Grillo and Gross were able to show that the rate of resorption of collagen could be reduced by controlled crosslinking with formaldehyde. They were also able to show that the immune response to reconstituted collagen implants was minimal. Grillo, H. C. and Gross, J., *J. Surg. Res.*, 2, 69 (1962).

Enzymatically modified collagen has been prepared and evaluated by Rubin and Stenzel who showed that this treatment does not evoke as much cellular response as the untreated material. The explanation for this variation in behavior is that the enzyme used (proctase) effectively removes the telopeptides from the collagen molecule without destroying the native molecular structure. Rubin, A. L. and Stenzel, K. H., in *Biomaterials* (Stark, L. and Aggarwal, G., eds.), Plenum Press, N. Y. (1969). The use of reconstituted collagen sheets has not eliminated the problems of lysis, infection and prevention of tissue ingrowth and vascularization encountered by use of other approaches.

SUMMARY OF THE INVENTION

This invention relates to a multilayer membrane which has properties necessary for artificial skin.

A first layer is nonimmunogenic, insoluble in the presence of body fluids, and nondegradable in the presence of body enzymes. Preferred materials for the first layer comprise crosslinked collagen-mucopolysaccharide composites, which are synthesized by intimately contacting collagen with a mucopolysaccharide and subsquently crosslinking the resultant product. Suitable collagens can be derived from a number of animal sources, and suitable mucopolysaccharides include, but are not limited to, chondroitin 4-sulfate, chondroitin 6-sulfate, dermatan sulfate, keratan sulfate, heparan sulfate, heparin, and hyaluronic acid.

Crosslinking can be achieved by chemical, radiation, dehydrothermal or any other suitable technique. A suitable chemical technique is aldehyde crosslinking, but other chemical crosslinking reactants are equally suitable. Dehydrothermal crosslinking, which is preferred, is achieved by reducing the moisture level of the composites to a very low level, such as by subjecting the composite material to elevated temperatures and high vacuum. Dehydrothermal crosslinking eliminates the necessity to add, and in the case of toxic materials such as aldehydes, to remove unreacted crosslinking agents; dehydrothermal crosslinking also produces composite materials containing a wider range of mucopolysaccharide content.

The products of such syntheses are believed to be comprised of collagen molecules or collagen fibrils with long mucopolysaccharide chains attached to them. Crosslinking appears to anchor the mucopolysaccharide chains to the collagen so that they will not elute or otherwise become disengaged. Mechanically, these materials can be thought of as analogous to fiber reinforced composite materials wherein collagen is the fiber and mucopolysaccharide is the matrix; therefore, these materials are sometimes referred to herein as composite polymeric materials.

Crosslinked collagen-mucopolysaccharide composites have been found to retain the advantageous properties of native collagen. Additionally, such materials can be synthesized to be non-antigenic, nondegradable by collagenase and other enzymes, and insoluble in the presence of body fluids. Additionally, such composites can be synthesized to have ultimate tensile strengths, elongations at break, and other mechanical properties particularly desired for artificial skin grafts and wound dressings.

A moisture transmission control layer is adherently bonded to the first layer. This control layer is formed from a nontoxic material which provides the overall membrane with a moisture flux of about 0.1 to about 1 mg/cm$^2$/hr., which is approximately the moisture flux of normal skin. Suitable materials for the moisture transmission control layer include synthetic polymers such as silicone resins, polyacrylate or polymethacrylate esters or their copolymers, and polyurethanes.

Because of their unique combination of layers, the membranes described herein fulfill the functions required of artificial skin or wound dressings. The rate of body moisture loss and heat loss from the damaged skin area is controlled to levels close to those with normal skin. Additionally, bacterial infection is prevented by these membranes and the wound area is protected from mechanical abrasion or other wear. Importantly, membranes formed from a first layer of a crosslinked Collagen-mucopolysaccharide composites also provide a template for:

1. the ingrowth and proliferation of cells from the subcutaneous tissue underlying damaged skin area or from epidermal tissue adjacent to the damaged skin area; the ingrowth and proliferation of capillaries and other blood vessels connected with the underlying subcutaneous tissue or other tissue adjacent to the damaged area; and the development of new dermal tissue and epidermal tissue. These membranes also are capable of controlling the intensity, direction and rate of contractures associated with the healing process.

BRIEF DESCRIPTION OF THE FIGURE

The FIGURE illustrates schematically a multilayer membrane as described herein.

DESCRIPTION OF PREFERRED EMBODIMENTS

The multilayer membranes described herein have at least two layers of different materials. As illustrated in the FIGURE, there is a first layer 10. Since layer 10 comes into direct contact with the subcutaneous tissue or wound bed, there are three essential characteristics required of this layer. These are: insolubiity in body fluids; nondegradability upon contact with body enzymes; and nonimmunogenicity. These multilayer membranes also include at least one additional layer, which has the primary function of controlling the moisture flux for the overall membrane. Thus, moisture transmission control layer 12 is illustrated in the FIGURE as being directly bonded to the first layer. It should be understood, however, that additional layers can be added on top of layer 12 or between first layer 10 and moisture control layer 12 as long as such additional layers do not interfere with the essential functions of these layers.

In addition to the aforementioned essential properties for the first layer, there are other properties which are highly desirable for this layer to possess.

One such desirable property relates to wetting and adhesion properties. It is desirable to form the first layer from a material which initially wets and adheres to a wound bed. These are prerequisites to the elimination of air pockets which may later become sites of bacterial proliferation. The immediate development of a moderately strong bond between a membrane graft and host tissue protects the graft from being displaced over the wound bed due to shear forces during bandaging or healing and thereby prevents air pockets from being formed. Therefore, it is preferred to use a material for the first layer which will quickly form a bond with host tissue having a shear strength of at least about 10 psi, and even more preferably of at least about 100 psi.

Further, it is desirable to use a material for the first layer which has mechanical properties which allow the membrane to "drape" over a wound bed and yet which resists tear during use. Thus, materials with a Young's modulus between about 100 and about 1000 psi, and an ultimate tensile strength of at least 100 psi, are preferred.

Epithelization of the membrane graft/epidermal tissue boundary provides a natural barrier to infection. Such a barrier can be formed by an epithelial sheet advancing over or through the graft, as illustrated in the FIGURE. Because of this, it is desirable to use a material for the first layer which allows epithelization velocities of at least about 0.1 mm/day.

Infiltration of the multilayer graft with endothelial cells, fibroblasts and other cells, as illustrated in the FIGURE, is a prerequisite for a graft that will serve as a template for neodermal tissue generation. Therefore, materials are preferred if they allow an infiltration rate of such cells of at least about 0.1 mm/day. This would allow cells to traverse about one-half of the thickness of a graft membrane having a typical thickness of 2 mm in 10 days or less.

Preferred materials for the first layer are crosslinked collagen-mucopolysaccharide materials. These are synthesized by contacting collagen with a mucopolysaccharide and subsequently crosslinking the resultant collagen-mucopolysaccharide product.

Collagen is a major protein constituent of connective tissue in vertebrate as well as invertebrate animals. It is often present in the form of macroscopic fibers which can be chemically and mechanically separated from non-collagenous tissue components. Collagen derived from any source is suitable, including collagen which is insoluble or is soluble in neutral, acidic and basic aqueous solutions, as well as those collagens which are commercially available. Typical animal sources include calfskin, bovine Achilles tendon and cattle bones.

The term mucopolysaccharide describes hexosamine-containing polysaccharides of animal origin. Another name often used for this class of compounds is glycosaminoglycans. Chemically, mucopolysaccharides are alternating copolymers made up of residues of hexosamine glycosidically bound and alternating in a more-or-less regular manner with either hexuronic acid or hexose moieties. See Dodgson, K. S., and Lloyd, A. G., in *Carbohydrate Metabolism and its Disorders*, ed. by F. Dickens, et al., vol. 1, Academic Press (1968).

Some of the better known mucopolysaccharides derived from animals can be represented by the following structural formulas:

HYALURONIC ACID

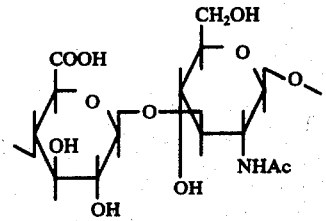

CHONDROITIN 4-SULFATE

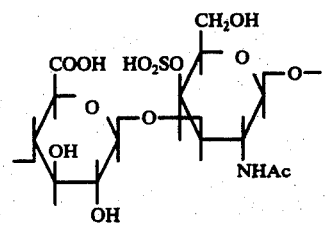

CHONDROITIN 6-SULFATE

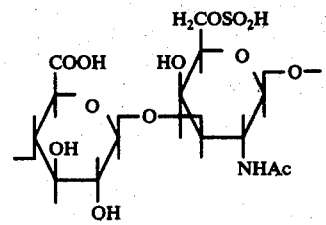

DERMATAN SULFATE

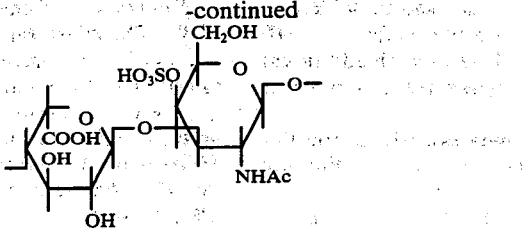

KERATAN SULFATE

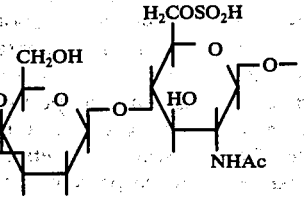

HEPARAN SULFATE

Other mucopolysaccharides are suitable for forming the composite materials described herein, and those skilled in the art will either know or be able to ascertain, using no more than routine experimentation, other suitable mucopolysaccharides. For a more detailed description of mucopolysaccharides, see the following reference, the teachings of which are hereby incorporated by reference: Aspinall, G. O., *Polysaccharides*, Permagon Press, Oxford (1970).

Typical sources of heparin include hog intestine, beef lung, bovine liver capsule and mouse skin. Hyaluronic acid can be derived from rooster comb and human umbilical cords, whereas both of chondroitin 4-sulfate and chondroitin 6-sulfate can be derived from bovine cartilage and shark cartilage. Dermatan sulfate and heparan sulfate can be derived from hog mucosal tissues while keratan sulfate can be derived from the bovine cornea.

Collagen can be reacted with a mucopolysaccharide in aqueous solutions which can be either acidic, basic or neutral. These reactions can be carried out at room temperature. Typically, small amounts of collagen, such as 0.3% by weight, are dispersed in a dilute acetic acid solution and thoroughly agitated. The polysaccharide is then slowly added, for example dropwise, into the aqueous collagen dispersion, which causes the coprecipitation of collagen and mucopolysaccharide. The coprecipitate is a tangled mass of collagen fibrils coated with mucopolysaccharide which somewhat resembles a tangled ball of yarn. This tangled mass of fibers can be homogenized to form a homogeneous dispersion of fine fibers and then filtered and dried. Collagen-mucopolysaccharide coprecipitation products have been studied by Podrazky, V., Steven, F. S., Jackson, D. S., Weiss, J. B. and Leibovich, S. J., *Biochim. Biophys. Acta.*, 229, 690 (1971).

Although the collagen-mucopolysaccharide reaction product coprecipitates from the aqueous medium from which it is formed, it has been found that the mucopolysaccharide component can dissolve in other aqueous solutions. This is particularly true for more concentrated aqueous salt solutions, such as body fluids. It is known, for example, that collagen-mucopolysaccharide coprecipitates are insoluble in 0.01M NaCl, somewhat soluble in 0.1M NaCl, and quite soluble in 0.4M NaCl — the physiological level is about 0.14M NaCl. Thus, these reaction products have only limited insolubility and are not suitable, per se, as candidate materials for the first layer of multilayer membranes suitable for use as synthetic skin.

While the coprecipitation method described supra is preferred, collagen and mucopolysaccharides can be reacted in other ways. The essential requirement is that the two materials be intimately contacted under conditions which allow the mucopolysaccharides to attach to the collagen chains. Another suitable technique is to coat collagen with mucopolysaccharide, such as by dipping articles formed from collagen, including sheets, films, and tubes, into a solution of mucopolysaccharide. A suitable variation of the latter technique involves prior coating with collagen of an article, sheet, film or tube fabricated from a non-collagenous material, such as a synthetic, natural or modified natural polymer, followed by dipping of the collagen-coated article, sheet, film or tube into the mucopolysaccharide solution. Still another suitable method is to intimately mix collagen with mucopolysaccharides, with each component in the form of a dry powder.

To those skilled in the art of forming sheets, films, tubes and other shapes or articles by techniques that are shown in the plastics, elastomerics and fiber-forming industries, it would be obvious that the collagen-mucopolysaccharide product prepared as described above could also be formed into sheets, films, tubes and other shapes or articles by such techniques.

To gain any significant increase in resistance to collagen resorption, it is necessary to have at least about 0.5% by weight of mucopolysaccharide bound to the collagen chains. The upper limit may be set by the available sites on collagen for mucopolysaccharide to attach. For composites wherein the mucopolysaccharide is chondroitin 6-sulfate, levels of about 28% by weight have been achieved; with hyaluronic acid, on the other hand, the upper limit achieved is about 25%.

Reaction with the mucopolysaccharides also provides collagen with another valuable property, i.e., inability to provoke an immune reaction (foreign body reaction) from an animal host. To convert collagen into a material which, when implanted, would not be recognized as a foreign body requires reacting it with at least about 1% by weight of mucopolysaccharide.

The degree of insolubility of the collagen-mucopolysaccharide products can be raised to the desired degree by crosslinking these materials. In general, any crosslinking method suitable for crosslinking collagen is also suitable for crosslinking these composite materials. Such crosslinking serves to prevent dissolution of mucopolysaccharide in aqueous solutions thereby making the materials useful for surgical prostheses, etc.

Crosslinking also serves another important function by contributing to raising the resistance to resorption of these materials. The exact function of crosslinking is not understood in this regard, but it may be that crosslinking anchors the mucopolysaccharide units to sites on the collagen chain which would normally be attacked by collagenase.

It has been found that the crosslinked composites should have an $M_c$ (number average molecular weight between crosslinks) of between about 800 and about 60,000. Materials with $M_c$ values below about 800 or above about 60,000 suffer significant losses in their mechanical properties. Composites with an $M_c$ of between about 5000 and about 10,000 appear to have the best balance of mechanical properties, and so are preferred materials.

Crosslinking can be achieved by many specific techniques with the general categories being chemical, radiation and dehydrothermal methods. An advantage to most crosslinking techniques contemplated, including glutaraldehyde crosslinking and dehydrothermal crosslinking, is that they also serve in removing bacterial growths from the materials. Thus, the composites are being sterilized at the same time that they are crosslinked.

One suitable chemical method for crosslinking the collagen-mucopolysaccharide composites is known as aldehyde crosslinking. In this process, the materials are contacted with aqueous solutions of aldehydes, which serve to crosslink the materials. Suitable aldehydes include formaldehyde, glutaraldehyde and glyoxal. The preferred aldehyde is glutaraldehyde because it yields the desired level of crosslink density more rapidly than other aldehydes and is also capable of increasing the crosslink density to a relatively high level.

Unreacted aldehydes should be removed from the collagen-mucopolysaccharide materials since residual aldehydes are quite toxic. It has been noted that immersing the composites in aldehyde solutions causes partial removal of the polysaccharide component by dissolution thereby lessening the amount of polysaccharide in the final product.

Other chemical techniques which are suitable include carbodiimide coupling, azide coupling, and diisocyanate crosslinking.

A preferred crosslinking method is referred to herein as a dehydrothermal process. In dehydrothermal crosslinking, it is not necessary to add external crosslinking agents. The key is to remove a large percentage of the water in the product to be crosslinked. The amount of water which must be removed will vary with many factors, but, in general, sufficient water to achieve the desired density of crosslinking must be removed. Thus, the collagen-mucopolysaccharide product can be subjected to elevated temperatures and/or vacuum conditions until the moisture content is reduced to extremely low levels. In the absence of vacuum, temperatures above about 80° C, and preferably above 90° C, can be used. At 23° C, vacuum of at least about $10^{-5}$mm. of mercury, and preferably below $10^{-6}$mm. of mercury, are suitable. Elevated temperature and vacuum can be also used in combination; this, in fact, is the most expeditious route and is therefore preferred. With a vacuum of at least about $10^{-5}$mm. of mercury, it is preferred to use a temperature of at least about 35° C. In general, the materials are subjected to the elevated temperatures and vacuum conditions until the degree of insolubility desired is obtained. The higher the temperature, the lower is the vacuum required to arrive at a given crosslink density; and vice versa. A typical crosslinking process to attain an $M_c$ between about 5,000 and 10,000 would involve subjecting the collagen-mucopolysaccharide to a temperature of 95° C and a vacuum of 0.01mm. of mercury for 24 hours. This dehydrothermal crosslinking process overcomes certain disadvantages of the aldehyde crosslinking method and produces composites having relatively large amounts of mucopolysaccharide strongly bound to the collagen chain.

The exact mechanism operating in the dehydrothermal crosslinking process is not known. However, it may be either an amide condensation involving $\epsilon$-amino groups from collagen and carboxyl groups from the mucopolysaccharide component, or esterification involving carboxyl groups from collagen and hydroxyl groups from the mucopolysaccharide or esterification involving carboxyl groups from the mucopolysaccharide component and hydroxyl groups from collagen. Possibly all three mechanisms are involved to some extent. For a more detailed description of dehydrothermal crosslinking, see Yannas, I. V. and Tobolsky, A. V., "Crosslinking of Gelatin by Dehydration," *Nature*, vol. 215, No. 5100, pp. 509–510, July 29, 1967, the teachings of which are hereby incorporated by reference.

Crosslinked collagen-mucopolysaccharide composite materials are described in detail in the copending application entitled "Crosslinked Collagen-Mucopolysaccharide Composite Materials," by Yannas, Gordon, Huang and Silver, Ser. No. 596,111, filed on July 15, 1975 the teachings of which are hereby incorporated by reference.

Crosslinked collagen-mucopolysaccharide composites can be synthesized which have all of the essential properties required for the first layer, and also possess many, if not all, of the desired properties thereof.

The immunogenicity of collagen-mucopolysaccharide composite materials prepared as described supra is negligible, as shown following implantation and grafting studies with guinea pigs. When implanted subcutaneously, or used as skin grafts, these materials elicit from the host tissue a mild inflammatory response represented by a few polymorphonuclear leukocytes and monocytes. Lumphocytes are typically not observed either in the interior of these implanted or grafted materials or in the surrounding tissue. Collagen fiber synthesis has been frequently observed to occur at the graft-/host tissue interface, with formation of fibrous bridges between the adjacent surfaces and a resulting mechanical anchoring of the implant on the host tissue. The collagen-mucopolysaccharide composites, therefore, not only posses very weak immunogenicity but, in addition, appear to be media which encourage fibroblast migration and collagen synthesis.

A mechanochemical method was used to provide an in vitro measure of resistance to enzymatic degradation for the composites. This method involves stretching the composite material to a fixed extension in the presence of a solution of collagenase and measuring the rate of relaxation of the force induced on the material. Using bacterial collagenase, an exponential decrease in force with time was invariably observed. The negative slope of the linear plot of logarithmic force versus time $(1/\tau)$ is taken as a measure of rate of enzymatic degradation. The method produces data for collagen fibers consistent with other known data obtained by subcutaneous implantation in guinea pigs. Yannas, I. V., Burke, J. F., Huang, C. and Gordon, P. L., Correlation of In Vivo Collagen Degradation Rate With In Vivo Measurements, *J. Biomed, Materials Research*, in press, 1975. Using this method, it has been found that enzymatic degradation of collagen is strongly suppressed for crosslinked composites wherein the mucopolysaccharide contains a sulfate group. These findings correlate very well with in vivo studies with guinea pigs.

Particularly preferred first layer materials are crosslinked collagen-mucopolysaccharide composites containing between about 6% and about 15% of a sulfate-containing mucopolysaccharide and crosslinked to an $M_c$ value of between about 5,000 and about 10,000. Chondroitin 6-sulfate forms especially outstanding composites.

As described supra, the multilayer membranes also include a second layer which has the primary function of controlling the moisture flux for the overall membrane, as illustrated in the FIGURE.

Moisture flows out of normal, undamaged human skin (forearm) at rates in the order of 0.5 mg/cm$^2$/hr. Spruit, D. and Malten, K. E., *Dermatologica*, 132, 115 (1966). Following removal of the stratum corneum (possibly of a part of the stratum granulosum) by "stripping" with adhesive tape, the moisture loss increases by 100–200 times to 60–100 mg/cm$^2$/hr. This value is comparable to the evaporation rate at a free water surface, obtained under equivalent experimental conditions as above which is 85 mg/cm$^2$/hr. Spruit, D., *54* (1970)

Clearly, the stratum corneum is the major barrier of the skin against water loss since its removal leads to a rate of moisture loss which is almost identical to that occurring at the surface of free water. The efficiency of this moisture barrier is independent of the direction of water flow since it has been shown (by use of tritiated water) that the rate of permeation of liquid water through forearm skin is 0.6 mg/cm$^2$/hr when the water is applied at the outside of the skin. Downes, A. M. Sweeney, T. M. and Matoltsy, A. G., *J. Invest. Derm.*, 49, 230 (1967).

In the design of a membrane useful as artificial skin, an effort has to be made to duplicate the value of moisture transmission rate for normal skin. Should the normal transmission rate values be exceeded, the host tissue in the neighborhood of the graft as well as the graft itself will become dehydrated; if, on the other hand, much lower transmission rates obtain, edema may result. These considerations apply, of course, only under conditions of intimate graft-host tissue contact; should substantial air pockets form at the interface, significant amounts of moisture from the host tissue may escape to the atmosphere without passing through the graft.

Therefore, a moisture transmission control layer is formed from a material which provides a moisture flux per unit area for the overall membrane of at least about 0.1 to about 1 mg/cm$^2$/hr. Preferably, the moisture flux per unit area is about 0.3 to about 0.5 mg/cm$^2$/hr., which is approximately the range of human forearm skin. These values are obtained by an appropriate combination of thickness and water transmission properties.

The other essential property of this layer is that it be nontoxic. The material should contain no toxic substances capable of diffusing out into tissues contacting a multilayer membrane graft or capable of being extracted therefrom. Also, the material should be capable of resisting enzymatic degradation or other degradation resulting from contact with other layers of the membrane or with tissue which degradation might lead to the production of substances that are toxic to neighboring tissue.

As is the case with the first layer, there are several other desirable properties for the layer which primarily controls the moisture flux. Thus, it is desirable that the moisture-control layer adhere to the wet surface of the firt layer with a bond shear strength of at least about 10 psi, and preferably about 100 psi. It also is desirable that it have mechanical properties of: Young's modulus in the range of from about 100 to 1,000 psi; ultimate tensile strength of from about 100 to about 1,000 psi; and elongation at break of from about 20 to about 100%.

Additionally, it is advantageous if the moisture control layer is capable of being sterilized, i.e., of being subjected to physical or chemical treatment that kills bacteria and bacterial spores on its surface. Suitable sterilization techniques include dry heat, exposure to ethylene oxide, irradiation, immersion in glutaraldehyde solution, etc.

It is also desirable that the material constituting the moisture-control layer, when applied to the first layer in liquid or semiliquid form, not penetrate into the first layer more than about 20% by weight, of the final semisolid or solid-like, cured form of the first layer. Further penetration is deleterious because the porosity of the collagen-mucopolysaccharide layer would be seriously decreased and, consequently, moisture transmission through and repair mechanisms occurring into the latter, such as tissue ingrowth, vascularization, etc., would be impaired.

Finally, it is also desirable that the moisture-control layer be capable of resisting any degradation process, caused by its proximity or contact with adjacent layers or tissue, which would lead to significant impairment of the aforementioned biological, mechanical and chemical properties.

Certain synthetic polymeric materials satisfy the essential, and many of the desirable, properties of the moisture control layer. Among these are: silicone polymers, such as Silastic Medical Adhesive (Dow Corning), a mixture of an hydroxyl terminated silicone polymer and methyl triethoxy silane which moisture-cures into a flexible, tough layer that adheres very well to first layer materials such as crosslinked collagen-mucopolysaccharide composites; polyacrylate or polymethacrylate esters or their copolymers such as an acrylic rubber latex formed from an ethyl acrylate-acrylic acid copolymer which forms a flexible film on top of first layer materials and which contains carboxylic acid groups capable of reacting with hydroxyl groups present in crosslinked collagen-mucopolysaccharide materials to form strong bonds; polyurethanes such as a reaction product of excess toluene diisocyante with a mixture of diols and triols to give a reactive, moisture-curing prepolymer capable of forming an elastomeric layer on crosslinked collagen-mucopolysaccharide composites and having chemical groups which react with amino groups or hydroxyl groups in such composites. Those skilled in the art will recognize or be able to fine, using no more than routine experimentation, other materials which are suitable for the moisture control layer.

Silicone polymer is preferred as the moisture control layer. It is available as a non-toxic product in a carefully controlled medical grade. Its flow properties are of thixotropic nature, permitting uniform application by knife blade onto the surface of collagen-mucopolysaccharide composite layer with controlled penetration into the latter. Curing can be done at 100% relative humidity, thereby avoiding dehydration of the lower layer, consisting of the collagen-mucopolysaccharide composite, and preventing deformation of the multilayered structure. Silicone polymer cures by rection with hydroxyl groups, and since hydroxyl groups are present in the layer consisting of the collagen-mucopolysaccharide composite, sufficient covalent bonding between layers is possible to form a satisfactory bond thereby obviating the need for an adhesive material to bond the silicone polymer layer to the layer consisting of the collagen-mucopolysaccharide composite.

Multilayer systems can also be made by using a moisturecuring silicone elastomer as the agent bonding the collagen-mucopolysaccharide layer to another material. By applying a thin film (1–2 thousandths of an inch) over a film prepared from synthetic polymers such as the segmented polyurethanes, hydroxyethyl methacrylate and other "hydrogels," polyethylene terephthalate and polytetafluoroethylene or from modified natural polymers such as cellulose acetate or from natural polymers such as elastin (the fibrous, insoluble, noncollagenous protein found in connective tissue such as the thoracic aorta and ligamentum muchae), a multicomponent composite can be obtained by curing at room temperature at 100% relative humidity for 16–24 hours.

It mechanical reinforcement is desired, a layer of gauze or other fabric or mesh could be usefully employed. Cotton or other textile mesh can be incorporated as a reinforcing mechanism by placing the textile material over the collagen-mucopolysaccharide composite and applying the Silastic silicone over the mesh onto the collagen-mucopolysaccharide surface by knife coating. Curing at room temperature and 100% relative humidity overnight (16–24 hours) can result in a reinforced composite which is somewhat stiffer than one without the mesh but with substantially improved tensile strength.

The optimum thickness of a synthetic skin is related to the following parameters: (1) thickness of the skin to be replaced; (2) nature of wound and dimensions; (3) thickness of top layer required to control moisture flux; and, (4) relation of suturability to thickness.

In the case of full thickness guinea pig skin, the average thickness of the excised skin is 25–30 mils. Composites used to replace guinea pig skin comprise a layer of collagen-chondroitin 6-sulfate with a thickness of 15 mils and a layer of silicone polymer of 5 mils. This combination provides moisture flux rates equal to that of the guinea pig skin and is easily sutured to the perimeter of the wound bed in grafting tests.

The lowest attainable limit of thickness for the collagen-mucopolysaccharide layer is dependent upon the particle size of the collagen-mucopolysaccharide composites and is typical in the range of 1.5 – 2.0 mils. The upper limit of thickness depends only upon the application contemplated and in practice are available up to indefinitely high levels depending upon the quantity of dispersion filtered through a given area of filter. Thickness as high as 100–200 mils are readily prepared by the process herein described, although for application as a skin substitute, the preferred range is 25–100 mils.

On the other hand, the thickness of the top layer would be dictated by the desired moisture flux and the moisture vapor transmission properties of the polymer used to form the top layer. In the case of Silastic Medical Grade silicone, a 5-mil thick silicone film layered onto a 15-mil thick layer of collagen-mucopolysaccharide composite is a typical multilayer artificial skin having the desired range of moisture flux. For polymers with lower rates of moisture vapor transmission rate, the moisture-control layer would have to be reduced in thickness proportionally.

The multilayer membranes described herein are useful as dressings for the treatment of burns, cuts, lacerations, abrasions and other such conditions which involve injury or destruction of skin by mechanical, thermal, chemical or other external insult by local or systemic disease. Also, the membranes themselves can be used as artificial grafts wherein they replace functions of normal skin and provide a template for cellular regeneration.

The invention is further and more specifically illustrated by the following examples.

EXAMPLE 1

Preparation of Collagen Dispersions and Mucopolysaccharide Solutions

The collagen used was prepared by precutting limed calf hides into strips ⅜ inch wide and then into thin pieces. These thin pieces of hide were contacted with three parts of water containing 0.3% propionic acid and 0.1% benzoic acid. Equilibrium was established after four hours at which time the solution had a pH approaching 5.3. The collagen slurry was separated from the water and ground to products of different particle sizes and structures with a centrifugally acting cutter-grinder. The calf hide collagen slurry (1:1 water-to-hide weight ratio) had a gelatin content of about 2%. Additionally, it contained about 0.41% calcium and about 0.041% magnesium. Physically, the slurry was composed of highly entangled fibrillar aggregates.

The calf hide collagen slurry was purified by a repeated precipitation from a turbid dispersion in 0.05 M acetic acid with 0.2 M sodium dihydrogen diphosphate, $NaH_2PO_4$. After purification, collagen was dispersed in 0.05 M acetic acid or in a citric acid-buffer solution at pH 3.2 (0.1 M citric acid, 0.2 M sodium dihydrogen diphosphate). The dispersion was thoroughly homogenized in a Waring Blender until the absorbance at 440 millimicrons of a 0.3% (W/V) collagen dispersion was about 0.5 as measured on a spectrophotometer (Coleman Junior II A, Maywood, Illinois). The resulting collagen dispersions were stored at 4° C until further processing was required.

Mucopolysaccharide solutions were prepared from sodium heparin, hyaluronic acid and chondroitin 6-sulfate. Sodium heparin, from hog intestinal mucosa, 143 U.S.P. units of activity per milligram, was purchased from Abbott Laboratories, North Chicago, Illinois. Hyaluronic acid, from rooster comb was prepared by the method of Swann, D. A., *Biochim. Biophys. Acta*, 156, 17 (1968). The resulting hyaluronic acid contained 47.1% hexuronic acid and 42.6% hexosamine.

Chondroitin 4-sulfate from bovine nasal cartilage was prepared by the method described by Roden, L., Baker, J. R., Cifonelli, J. A. and Mathews, M. B., in *Methods of Enzymology*, V. Ginsburg, ed., vol. 28B, Academic Press, New York, p. 73. Heparan sulfate and dermatan sulfate were both extracted from hog mucosal tissues and purified by the methods described by Cifonelli, J. A. and Roden, L., *Biochemical Preparations*, 12, 12 (1968).

Chondroitin 6-sulfate, from shark cartilage — Grade B, was purchased from Calbiochem, San Diego, California. It contained 2.66% nitrogen, 37.2% glucuronic acid and 5.61% moisture.

Heparin, hyaluronic acid, chondroitin 4-sulfate, heparan sulfate, dermatan sulfate and chondroitin 6-sulfate were dissolved (1% W/V) in a citric acid-phosphate buffer pH 3.2. The mucopolysaccharide solutions were stored at 4° C.

EXAMPLE 2

Preparation of Collagen-Heparin and Collagen-Hyaluronic Acid Coprecipitates

Collagen 0.3% (W/V) dispersed in 0.05 M acetic acid was thoroughly agitated with a Teflon stirrer at 23° C. While the dispersion was mixing, heparin or hyaluronic acid 1% (W/V) in 0.05 M acetic acid was added drop wise from a buret at the rate of about 0.1 ml. per second. The addition of mucopolysaccharide caused collagen to coprecipitate forming a tangled mass of collagen fibrils coated with mucopolysaccharide which somewhat resembled a tangled ball of yarn. When 90% by weight of collagen was coprecipitated in this manner with 10% by weight mucopolysaccharide, a systematic mass balance showed that about 95% of the original mucopolysaccharide was coprecipitated.

After coprecipitation, the tangled mass of fibrils was homogenized in a Waring Blender until the fibrils were about 1 mm. in length. The mixture of fibrils in 0.05 M acetic acid separated into two phases when left unagitated for more than 5 minutes, so that mixing was required before filtration. Filtration was performed by filtering the collagen-mucopolysaccharide dispersion under vacuum through a Buchner funnel containing Schleicher and Schuell (Keene, New Hampshire) filter paper No. 576. The coprecipitate was allowed to dehydrate under atmospheric conditions until the moisture content was about 20% by weight.

EXAMPLE 3

Preparation of Collagen-Chondroitin 6-sulfate Coprecipitates

Collagen 0.3% (W/V) dispersed in a citric acid-phosphate buffer solution pH 3.2 at 23° C was coprecipitated with a 1% (W/V) chondroitin 6-sulfate buffer solution pH 3.2 at 23° C. The coprecipitate was homogenized, filtered and allowed to dry in the atmosphere as described in Example 2.

EXAMPLE 4

Aldehyde Crosslinking of a Collagen-Chondroitin 6-sulfate Composite

Coprecipitated collagen-chondroitin 6-sulfate as prepared in Example 3 was crosslinked by immersing it in a 0.02 M solution of glutaraldehyde. This treatment effectively immobilized a fraction of the polysaccharide component on the collagen fibrils or molecules. Crosslinking was evidenced by the inability to remove the polysaccharide from the aldehyde-treated film by prolonged washing with a phosphate buffer solution containing 0.4 M sodium chloride, pH 7.4, which is a well known solvent of chondroitin 6-sulfate. Unreacted aldehydes were removed by treatment with a solution of 5,5-dimethyl-1,3-cyclohexane dione (dimedone). Evaporation of the water left behind a film containing up to about 10% by weight polysaccharide.

EXAMPLE 5

Dehydrothermal Crosslinking of Collagen-Chondroitin 6-Sulfate

The product of Example 3 was placed in a vacuum oven and exposed to a temperature of 115° C and a vacuum of at least 0.3mm. Hg. for 48 hours. At the end of this treatment, less than 10 weight percent of the polysaccharide originally incorporated into the film could be removed by 48-hour immersion in distilled water, a solvent for chondroitin 6-sulfate.

EXAMPLE 6

Hexosamine Analysis and Molecular Weight Between Crosslinks

Since mucopolysaccharides are hexosamine-containing polymers, the level of hexosamine is directly related to the amount of a specific mucopolysaccharide in a composite material. Once a relationship is established between the hexosamine content and weight for each individual mucopolysaccharide, the determination is straightforward. This analysis is described in detail by Huang, C., Sc. D. Thesis, Mech. Eng. Dept., M.I.T., Cambridge, Mass., Chaps. 3, 4 (1974). The method is summarized as follows. A known weight of a vacuum dried (48 hours at 105° C) composite is placed in a 5 ml. ampule and 1 ml. of 8 M HCl is added. The ampule is evacuated and flushed with nitrogen gas followed by sealing under vacuum. Hydrolysis is initiated when the ampule is placed in a circulating air oven at 95° C. After 4 hours at 95° C, the ampule is cooled with tap water to 10° C. The contents of the tube are then evaporated to dryness at 40° C until only the dry hydrolyzate remains. The hydrolyzate is dissolved in distilled water to give a concentration of about 50–150 mg. of mucopolysaccharide per ml. of water. One ml. of the hydrolyzate solution is added to 1 ml. of an 8% (V/V) solution of acetylacetone in 1 M Na$_2$CO$_3$. After heating at 95° C for 1 hour, hexosamine contained in the hydrolyzate reacts with acetylacetone in alkaline solution to form derivatives of pyrrole. Upon cooling the solution to 10° C. 5 ml. of 95% ethanol and 1 ml. of Ehrlich reagent (prepared by dissolving 1.33g. of p-dimethylamino-benzaldehyde, DAB, in 50 ml. of 6 M HCl to which 50 ml. of 95% ethanol is added) are added followed by thorough mixing. The reaction between DAB and derivatives of pyrrole results in the formation of a chromophore which colors the product an intense red. After the mixture is allowed to stand for 2 hours, the absorbance is measured at 527 millimicrons against a reagent blank using a Coleman Junior II A spectrophotometer. The results of the analysis are compared to standard calibration curves for each mucopolysaccharide.

The results of hexosamine analysis on several crosslinked collagen-mucopolysaccharide materials prepared by the methods of previous Examples are presented in Table I. The mucopolysaccharide content before crosslinking was determined to be about 10% for each composite listed in Table I. It appears that during glutaraldehyde crosslinking and subsequent washing steps, large quantities of mucopolysaccharide were lost. This implies that the solubility of uncrosslinked mucopolysaccharides is high in the aqueous glutaraldehyde solution in which the former are immersed for the purpose of crosslinking them. For the dehydrothermally crosslinked composites, only 10%, at most, of a mucopolysaccharide was eluted, versus up to 61% for the glutaraldehyde process.

The mechanical properties of the composite materials is strongly influenced by the number of crosslinks per polymer chain. The molecular weight between crosslinks (Mc) is inversely proportional to the number of crosslinks per unit volume. By measuring the stress-strain behavior of thermally denatured collagen-mucopolysaccharide composites, values of $M_c$ can be determined. The technique is described by Treloar, L. R. G., The Physics of Rubber Elasticity, Second Edition, Clarendon Press (1958). A summary of experimental results for several collagen-mucopolysaccharide composites is also presented in Table I.

TABLE I

| Material | Crosslinking | % MPS | $M_c$ (± 10%) |
|---|---|---|---|
| Collagen | G (24, 7.4) | 0.0 | 1,500 |
| Collagen-H | G (24, 3.2) | 5.7±1.2 | 9,400 |
| Collagen-H | G (48, 7.4) | 5.5±1.3 | 1,200 |
| Collagen-H | G (24, 3.2 24, 7.4) | 4.0±1.0 | 1,800 |
| Collagen-H | D (48, 90° C) | 9.7±1.0 | 2,800 |
| Collagen-CS-6 | G (24, 3.2) | 3.9±.3 | 6,800 |
| Collagen-CS-6 | D (48, 90° C) | 9.6±1.1 | 1,200 |
| Collagen-HA | G (24, 7.4) | 2.3±.4 | 2,200 |
| Collagen-HA | D (48, 90° C) | 9.0±.5 | 2,500 |

G = Glutaraldehyde at 23° C (hours, pH)
D = Dehydrothermal (hours, temp.)
H = Heparin
CS-6 = Chondroitin 6-sulfate
HA = Hyaluronic Acid

EXAMPLE 7

Composites Formed by Coating Collagen with Mucopolysaccharides

Mucopolysaccharide solutions were prepared by dissolving 40 mg. of the mucopolysaccharide in 20 ml. citric acid-phosphate buffer (pH 3.2). A length of an insoluble collagen film was then added to the mucopolysaccharide solution and maintained at a constant temperature of 37° C and allowed to incubate for about 24 hours. Glutaraldehyde was then added to the solution to give a resultant concentration of 0.025 M of aldehyde. The collagen was kept in this solution for another 24 hours and was subsequently transferred to a 0.025 M solution of glutaraldehyde maintained at a pH of 7.4. The latter step was done in order to insure efficient crosslinking of collagen. After 24 hours in the glutaraldehyde solution, the collagen fibers were rinsed three times with distilled water and transferred to a 0.2 weight percent solution of dimedone in order to remove excess, unreacted aldehydes. After another 24 hours in the dimedone solution, the fibers were rinsed five times with distilled water and kept in a citric acid-phosphate buffer solution at pH 7.4 at 4° C. The weight percent of mucopolysaccharide attached to the collagen was determined by hexosamine analysis. The molecular weight between crosslinks, $M_c$, was determined using the procedure described in Treloar, L. R. G., The Physics of Rubber Elasticity, 2nd ed., Clarendon Press (1958). The results are presented in Table II.

TABLE II

| Material | % MPS (±0.5) | $M_c$ (±500) |
|---|---|---|
| Collagen | 0 | 3800 |
| Collagen-CS-6 | 11.3 | 4100 |
| Collagen-CS-4 | 8.7 | 4000 |
| Collagen-HA | 8.2 | 4200 |
| Collagen-DS | 8.2 | 3900 |
| Collagen-H | 8.7 | 3800 |
| Collagen-KS | 10.5 | 3800 |

CS-6 = Chondroitin 6-sulfate
CS-4 = Chondroitin 4-sulfate
HA = Hyaluronic Acid
DS = Dermatan Sulfate
H = Heparin
KS = Keratan Sulfate

EXAMPLE 8

Enzymatic Degradation of Composites Formed from Collagen Coated with Mucopolysaccharide A study of the enzymatic degradation of composites formed by coating a mucopolysaccharide onto collagen fibers as described in Example 7 was made. The mucopolysaccharide-coated collagen films, in the form of tape, were extended to a strain of 4.0±0.5% in the presence of a solution of collagenase (40 units/ml.) and the force induced on the tape was recorded as a function of time. The force was found to be representable by a single negative exponential of the time and hence a plot of the logarithmic force versus time yields a straight line. The slope of the straight line yields $1/\tau$ — a value which is taken as a measure of the rate of enzymatic degradation of the collagen by the collagenase. The results are presented in Table III.

TABLE III

| Material | % MPS (±0.5) | $1/\tau \times 10^4$ (±0.07) (min$^{-1}$) |
|---|---|---|
| Collagen | 0 | 8.48 |
| Collagen-CS-6 | 11.3 | 1.46 |
| Collagen-CS-4 | 8.7 | 0.88 |
| Collagen-HA | 8.2 | 5.38 |
| Collagen-DS | 8.2 | 0.90 |
| Collagen-H | 8.7 | 0.98 |
| Collagen-KS | 10.5 | 1.10 |

EXAMPLE 9

Enzymatic Degradation of Composites Formed from Coprecipitated Collagen and Chondroitin 6-sulfate Crosslinked composites of collagen and chondroitin 6-sulfate prepared according to the method of Example 4 were tested for their susceptibility to collagenase degradation. The technique used is described in the previous Example except that the strain imposed was 20±2%. The results are presented in Table IV.

TABLE IV

| % CS-6 (±0.2) | $M_c$ (±1000) | $1/\tau \times 10^2$ (±0.009) (min$^{-1}$) |
|---|---|---|
| 0 | 15000 | 0.255 |
| 1.8 | 14000 | 0.149 |
| 3.0 | 12000 | 0.153 |
| 4.8 | 13000 | 0.093 |
| 6.5 | 11000 | 0.084 |
| 8.6 | 9000 | 0.049 |
| 11.2 | 10000 | 0.052 |
| 13.3 | 12000 | 0.047 |
| 14.9 | 11000 | 0.064 |
| 16.0 | 14000 | 0.067 |

EXAMPLE 10

Mechanical Properties of Crosslinked Collagen-mucopolysaccharide Composite Materials Mechanical testing was done on an Instron tester using a B-type load cell. Dumbell shaped specimens 0.25 in. wide and about 0.01 in. thick were prepared for each candidate material. The top end of the specimen was attached to the load cell of the Instron while the lower end was attached to the crosshead through a clamping device. The strain on the specimen was calculated based on the crosshead movement. All measurements were conducted at a constant elongation rate of 50%/minute in tension at 37° C in a citric acid-phosphate buffer solution at pH 7.4.

Values of the force per unit area at rupture or ultimate tensile stress (U.T.S.), tangent to the stress-strain curve at 1% elongation (1% tangent modulus), elongation at break (E.B.), and work required to fracture (fracture work) were calculated for each material from the experimental stress-strain curve.

The results are presented in Table V below.

EXAMPLE 11

Increased Toughness due to Incorporation of Mucopolysaccharides

Comparison of specimens of collagen and crosslinked collagen-mucopolysaccharide composites at similar crosslinking levels suggests that the presence of the mucopolysaccharide significantly increases toughness of collagen. For example, the fracture work at similar levels of crosslinking from materials taken from the preceding Table are presented in Table VI below.

TABLE VI

| Material | % MPS | $M_c$ | Fracture Work (psi-%) ±10% |
|---|---|---|---|
| Collagen | 0.0 | 1200 | 1900 |
| Collagen-CS-6 | 9.6±1.1 | 1200 | 7100 |

As can be seen, the incorporation of about 10 weight percent chondroitin 6-sulfate in collagen increases the fracture work from about 1900 to about 7100 psi-%. Since the fracture work is maximal at an $M_c$ level of about 6500, it appears likely that a collagen-chondroitin 6-sulfate composite with about 10 weight percent of the mucopolysaccharide and an $M_c$ equal to about 6500 might possess a fracture energy greater than about 11,000 psi-%, the maximum fracture energy recorded for pure collagen under the conditions of these tests.

EXAMPLE 12

In Vivo Testing of Resorption Resistance of and Absence of Foreign Body Reaction Towards Composites In this Example, crosslinked collagen-mucopolysaccharide membranes, prepared both by coating collagen with each of the mucopolysaccharides as described in Example 7 as well as by coprecipitating collagen with each of the mucopolysaccharides as described in Examples 2 and 3, were implanted subcutaneously in guinea pigs as described below.

The collagen-mucopolysaccharide membranes had been sterilized by the process used to crosslink them. Immersion in an aldehyde bath (and, in particular, in a glutaraldehyde bath) over several hours as described in Example 4, is well-known as an effective means of chemical sterilization of a variety of materials prior to implantation or other surgical procedures. It is also known that exposure to temperatures in excess of 100°

TABLE V

| Material | Crosslinking | % MPS | $M_c$ | 1% Tangent Modulus (psi) | U.T.S. (psi) | E.B. % | Fracture Work (psi-%) ± 10% |
|---|---|---|---|---|---|---|---|
| Thoracic Aorta | — | — | — | 50 | 360 | 85 | 21,000 |
| Collagen | D (24, 90° C) | 0.0 | 9,200 | 235±50 | 380±10 | 40±10 | 8,800 |
| Collagen | D (48, 90° C) | 0.0 | 6,500 | 500±65 | 525±65 | 45±5 | 10,800 |
| Collagen | G (0.25, 7.4) | 0.0 | 3,800 | 950±100 | 334±51 | 15±2 | 5,000 |
| Collagen | G (24, 7.4) | 0.0 | 1,200 | 1800±200 | 359±11 | 10±1 | 1,900 |
| Collagen-H | G (24, 3.2) | 5.7±1.2 | 9,400 | 203±30 | 130±20 | 23±2 | 1,200 |
| Collagen-H | G (48, 3.2) | 5.7±1.2 | 6,800 | 475±70 | 160±20 | 16±2 | 1,100 |
| Collagen-H | D (48, 90° C) | 9.7±1.0 | 2,800 | 300±10 | 430±40 | 35±1 | 5,300 |
| Collagen-H | G (24, 7.4) | 5.5±1.2 | 1,800 | 1900±600 | 380±50 | 14±3 | 3,200 |
| Collagen-CS-6 | G (24, 3.2) | 3.9±0.3 | 6,800 | 343±120 | 130±10 | 21±2 | 1,100 |
| Collagen-CS-6 | G (48, 3.2) | 3.7±0.3 | 5,500 | 226±10 | 92±40 | 16±2 | 820 |
| Collagen-CS-6 | G (24, 7.4) | 3.5±0.3 | 2,500 | 253±92 | 133±30 | 11±3 | 650 |
| Collagen-CS-6 | D (48, 90° C) | 9.6±1.1 | 1,200 | 700±65 | 631±28 | 20±1 | 7,100 |
| Collagen-HA | D (48, 90° C) | 9.0±0.5 | 2,500 | 430±40 | 490±70 | 20±1 | 3,800 |

G = Glutaraldehyde at 23° C (hours, pH)
D = Dehydrothermal (hours, temp.)
H = Heparin
CS-6 = Chondroitin 6-Sulfate
HA = Hyaluronic Acid C over several hours is an alternative method of sterilization of materials that will be implanted or otherwise used in surgery. In addition, however, if the materials have been prepared considerably prior to grafting it is preferable to disinfect them just before grafting by immersion in 70/30 isopropanol/water for 24 hours at 23° C. Immersion in the latter medium does not alter either the crosslink density or other important structural features of collagen-mucopolysaccharide composites.

Subcutaneous implantation was carried out under aseptic conditions. White, Hartley, female guinea pigs, weighing approximately 400 grams, were used as subjects. For 7 days prior to implantation, a weight-change history was recorded for each animal. Shortly before implantation, the back of each animal was sheared with electric clippers over an area of ca. 6 cm × 5 cm and loose hair clippings were carefully removed with vacuum suction. The animal was then anesthesized by exposure to a mixture of oxygen and halothane, and its back was washed with 70/30 isopropanol/water.

A 1-inch incision was made on one side of the back of the animal. The incision was made such that a pocket between the dermis and the panniculus carnosus was created. The specimen was inserted into this pocket such that the whole specimen lay flat within the pocket. The incision was then sutured with nylon sutures. A total of about 5 to 6 stitches were made to close the incision. The procedure was repeated with the other side of the guinea pig back, using an identical specimen. The right side was subsequently used for histological studies while specimens from the left side were, after explanation, used for physicochemical characterization.

On the 4th, 10th, and 20th postimplantation days, the animals were sacrificed by placing them in a desiccator containing ether. From both the left and right implantation sites, $1\frac{1}{2} \times 1\frac{1}{2}$ inch squares of the tissues were cut below the subcutaneous layer such that the implanted specimens remained in the tissue. The tissue from the right side was placed in a 10% formalin solution and was subsequently used for histological studies as described below. The tissue from the left side was immersed in sterile Dulbecco's solution (50 ml) containing a few drops of chloroform (which acts as a bactericide) and stored under refrigeration for not more than 24 hours before the sample within it was removed.

Removal of the sample within the tissue was done by placing the tissue on the stage of a low powered microscope (equipped with a camera) and stripping the subcutaneous tissue from the dermis in such a way that the state of the sample within the tissue could be examined clearly with the microscope. This could be achieved by first cutting between the dermis and the subcutaneous tissue and gently separating the two parts by means of forceps. When viewed on the microscope, the state of the tissue and the sample embedded within it could be examined to reveal such features as the attachment of tissues to the implanted material. Removal of the sample from the tissue was done on the microscope stage by means of a forceps. After the materials had been removed from the tissue they were stored in Dulbecco's solution at 4° C until required to determine the following physicochemical properties:

1. The fractional weight change of the sample $\Delta W/W_i$. This was obtained by determining the dry weight of the samples (after dehydration at 105° C at a pressure of $10^{-3}$ mm. Hg. for 48 hours). The fractional weight change was then calculated as $$\Delta W/W_i = (W_e - W_i)/W_i$$

where $W_e$ = dry weight of the explanted sample, and $W_i$ = dry weight of the sample prior to implantation (the latter was determined by use of a control).

2. Tensile modulus, E, (in dynes/cm$^2$). This was obtained by the method described in Example 10 except that the modulus was determined as the slope of the straight portion of the stress-strain curve.

3. Molecular weight between crosslinks, $M_c$. This was measured as described in Example 4.

The characteristics of collagen-mucopolysaccharide specimens just before implantation as well as on the 4th, 10th and 20th days following implantation are presented in Table VII for materials that were prepared by coating collagen with various mucopolysaccharides prior to crosslinking and in Table VIII for materils prepared by coprecipitating collagen with mucopolysaccharides prior to crosslinking.

TABLE VII

COMPOSITES FORMED BY COATING COLLAGEN WITH MUCOPOLYSACCHARIDES. PRE- AND POST-IMPLANTATION PROPERTIES

| Properties | Preimplantation | In vivo residence time | | |
|---|---|---|---|---|
| | | 4 days | 10 days | 20 days |
| (1) Collagen | | | | |
| $\Delta W/W_i$ | 0.00±0.04 | −0.16±0.04 | −0.15±0.04 | −0.31±0.04 |
| $E \times 10^{-9}$ (dynes cm$^{-2}$) | 3.3±0.3 | 2.5±0.3 | 1.4±0.3 | 1.6±0.3 |
| $M_c \times 10^{-3}$ | 3.8±0.5 | 6.6±0.5 | 6.1±0.5 | 8.6±0.5 |
| (2) Collagen - Hyaluronic Acid | | | | |
| $\Delta W/W_i$ | 0.00±0.04 | −0.12±0.04 | −0.30±0.04 | −0.28±0.04 |
| $E \times 10^{-9}$ (dynes cm$^{-2}$) | 3.5±0.3 | 2.3±0.3 | 1.8±0.3 | −0.9±0.3 |
| $M_c \times 10^{-3}$ | 4.2±0.5 | 7.2±0.5 | 6.7±0.5 | 8.5±0.5 |
| (3) Collagen - Heparan Sulfate | | | | |
| $\Delta W/W_i$ | 0.00±0.04 | −0.06±0.04 | +0.04±0.04 | +0.38±0.04 |
| $E \times 10^{-9}$ (dynes cm$^{-2}$) | 4.0±0.3 | 3.5±0.3 | 3.8±0.5 | 3.6±0.5 |
| $M_c \times 10^{-3}$ | 3.8±0.5 | 4.6±0.5 | 4.7±0.5 | 4.5±0.5 |
| (4) Collagen - Heparin | | | | |
| $\Delta W/W_i$ | 0.00±0.04 | −0.02±0.04 | +0.08±0.04 | +0.32±0.04 |
| $E \times 10^{-9}$ (dynes cm$^{-2}$) | 4.2±0.3 | 3.9±0.3 | 4.2±0.3 | 4.3±0.3 |
| $M_c \times 10^{-3}$ | 3.8±0.5 | 4.3±0.5 | 4.3±0.5 | 3.6±0.5 |
| (5) Collagen - Dermatan Sulfate | | | | |
| $\Delta W/W_i$ | 0.00±0.04 | −0.09±0.04 | −0.05±0.04 | +0.31±0.04 |

TABLE VII-continued
COMPOSITES FORMED BY COATING
COLLAGEN WITH MUCOPOLYSACCHARIDES.
PRE- AND POST-IMPLANTATION PROPERTIES

| Properties | Preimplantation | In vivo residence time | | |
|---|---|---|---|---|
| | | 4 days | 10 days | 20 days |
| $E \times 10^{-9}$ (dynes cm$^{-2}$) | 3.9±0.3 | 4.0±0.3 | 3.0±0.3 | 3.1±0.3 |
| $M_c \times 10^{-3}$ | 4.0±0.5 | 4.9±0.5 | 5.3±0.5 | 5.2±0.5 |
| (6) Collagen - Chondroitin 6-sulfate | | | | |
| $\Delta W/W_i$ | 0.00±0.04 | −0.02±0.04 | −0.07±0.04 | +0.40±0.04 |
| $E \times 10^{-9}$ (dynes cm$^{-2}$) | 4.0±0.3 | 3.6±0.3 | 3.2±0.3 | 3.3±0.3 |
| $M_c \times 10^{-3}$ | 4.1±0.5 | 4.3±0.5 | 5.7±0.5 | 5.4±0.5 |

TABLE VII
COMPOSITES FORMED BY COPRECIPITATING
COLLAGEN WITH CHONDROITIN 6-SULFATE;
PRE- AND POST-IMPLANTATION PROPERTIES

| Properties | Preimplantation | In vivo residence time | | |
|---|---|---|---|---|
| | | 4 days | 10 days | 20 days |
| (1) Collagen | | | | |
| $\Delta W/W_i$ | 0.00±0.02 | −0.16±0.02 | −0.52±0.02 | −0.60±0.02 |
| $E \times 10^{-8}$ (dynes cm$^{-2}$) | 1.8±0.2 | 1.3±0.2 | 1.4±0.2 | 0.7±0.2 |
| $M_c \times 10^{-4}$ | 1.5±0.1 | 2.4±0.1 | 3.5±0.1 | 3.8±0.1 |
| (2) 1.8 wt-% Chondroitin 6-sulfate | | | | |
| $\Delta W/W_i$ | 0.00±0.02 | −0.20±0.02 | −0.28±0.02 | −0.39±0.02 |
| $E \times 10^{-8}$ (dynes cm$^{-2}$) | 1.9±0.2 | 1.5±0.2 | 1.0±0.2 | 1.0±0.2 |
| $M_c \times 10^{-4}$ | 1.4±0.1 | 1.8±0.2 | 2.9±0.2 | 3.0±0.2 |
| (3) 4.8 wt-% Chrondroitin 6-sulfate | | | | |
| $\Delta W/W_i$ | 0.00±0.02 | −0.04±0.02 | −0.08±0.02 | +0.33±0.2 |
| $E \times 10^{-8}$ (dynes cm$^{-2}$) | 1.8±0.2 | 1.5±0.2 | 1.2±0.2 | 1.3±0.2 |
| $M_c \times 10^{-4}$ | 1.3±0.1 | 1.5±0.2 | 2.0±0.2 | 2.4±0.2 |
| (4) 11.2 wt-% Chrondroitin 6-sulfate | | | | |
| $\Delta W/W_i$ | 0.00±0.02 | −0.04±0.02 | +0.18±0.2 | +0.65±0.2 |
| $E \times 10^{-8}$ (dynes cm$^{-2}$) | 1.9±0.2 | 1.6±0.2 | 1.6±0.2 | 1.7±0.2 |
| $M_c \times 10^{-4}$ | 1.0±0.1 | 1.4±0.1 | 1.3±0.1 | 1.6±0.1 |

It is clear from Table VII and VIII that in almost all cases where collagen was crosslinked with a mucopolysaccharide, either after being coated or coprecipitated with a mucopolysaccharide, the fractional weight loss was arrested indicating that the degradation of collagen had been effectively abolished by reaction with the mucopolysaccharide. The only exceptions were collagen coated with hyaluronic acid (a nonsulfated mucopolysaccharide) and collagen coprecipitated with only 1.8 weight percent chondroitin 6-sulfate; in the latter case, the fractional weight loss of collagen was delayed rather than arrested completely. In all other cases, an occasional very small initial weight loss, possibly due to deswelling of the implanted specimen, was reversed usually by the 10th day until, by the 20th day, the implant was heavier than when implanted. The increase in weight of the implant was found to be due to adherence of some of the surrounding tissue onto the implant as the latter was removed from the animal. The tissue adhering on the implant was analyzed and found to be constituted almost entirely of collagen, an observation showing that new collagen had been synthesized on the implant by cells in the surrounding tissues. Thus, not only did reaction with the sulfated mucopolysaccharides prevent degradation of collagen but also yielded a composite material capable of eliciting synthesis of new connective tissue on its surface by cells in the surrounding tissue.

The protection from resorption afforded to collagen by reaction with sulfated mucopolysaccharides is also evident in the prevention of the substantial decrease in modulus E and decrease in crosslink density (increase in $M_c$) which is observed with collagen itself or with a collagen-hyaluronic acid composite. The maintenance of E and $M_c$ to relatively steady levels (within the experimental uncertainty) up to 20 days of implanatation for composites of collagen and one each of the sulfated mucopolysaccharides is indicative of a crosslinked macromolecular network which remains intact for at least 20 days in the tissue of the living animal.

Histological studies were performed on the tissue/implant block removed from the right side of the animal on the 4th, 10th and 20th days. The standardized procedure used in preparing the specimens for histological examination was the following:

1. The tissue was fixed in 10% formalin (Fischer Scientific Co., NJ) for at least 24 hours at room temperature.

2. It was then dehydrated by sequential immersion in water-ethyl alcohol mixtures containing 50%, 70%, 85%, 95% and 100% alcohol, the time of immersion being 1 hour per mixture.

3. The tissue was then immersed in dioxane for 2 hours before it was embedded in a tissue-embedding medium (Paraplast, Mpt. 56°-57° C; Curtin Scientific Co., Houston, Texas). Embedding was achieved by first placing the tissue in the molten paraffin kept at 58° C for 4 hours, with hourly exchanges for the paraffin. Finally, the tissue was placed in a mould and embedded with a fresh supply of paraffin.

4. The paraffin block containing the tissue was then cooled to 0° C in a bath containing chipped ice for 20 minutes and was then mounted on a microtome (Minot Custom Microtome; International Equipment Co., Needham Heights, MA). Slices of the paraffin containing the tissue were microtomed to thicknesses of about 6μ.

5. The microtomed specimen was then mounted on a clear microscope slide and deparaffinization was achieved by immersing the mounted specimen in two exchanges of xylene for 3 minutes each.

6. The specimen was then rehydrated by sequential immersion in water-ethyl alcohol mixtures containing 100%, 95%, 85%, 70%, 50% and 0% alcohol, the time of immersion being 1 hour per mixture. The specimen was finally rinsed thoroughly with distilled water.

7. The specimen was then stained with hematoxylin for 5 minutes and rinsed briefly with distilled water. Excess stain was removed by rinsing the specimen with 0.5% acid alcohol (70% ethyl alcohol in concentrated hydrochloric acid). The acid alcohol was finally removed by rinsing the specimen and immersing it in water for ½ hour.

8. The specimen was then stained with 0.5% aqueous eosin for 3 minutes and then rinsed with 5 exchanges of water.

9. The specimen was dehydrated as in (2) above and then rinsed a few times with xylene.

10. It was then mounted on a clean cover slip with a permanent mounting medium (Harleco Synthetic Resin; Hartman-Leddon Co., Philadelphia, PA).

11. The cover slip containing the stained specimen was examined with a microscope.

The histological studies revealed that the extent and severity of chronic inflammation in the tissue surrounding the collagen implant decreased steadily as the content of chondroitin 6-sulfate in a series of implants based on coprecipitated collagen-chondroitin 6-sulfate composites increased in the range 1.8 to 11.2 weight percent. These results showed that while the collagen used in the composite materials provoked, when used by itself, a moderate immune response, reaction of the collagen with chondroitin 6-sulfate led to practically complete suppression of this immune response. These findings were also made when the implant was based on composite materials prepared by coating collagen with one of the sulfated mucopolysaccharides. In summary, the histological observations showed that the ability of implanted collagen to provoke a foreign body reaction from the animal host could be controlled and suppressed by reaction with one each of the sulfated mucopolysaccharides.

EXAMPLE 13

Preparation of Bilayer Composite Having A First Layer of Collagen-Chondroitin 6-Sulfate and a Second Layer Formed from a Silastic Silicone Polymer One hundred and fifty ml. of a 0.67% by weight collagen dispersion, prepared as in Example 1, was mixed with 50 ml. of citric acid-phosphate buffer, pH 3.2, containing 0.2 grams chondroitin 6-sulfate under high-speed stirring. The resultant precipitate was filtered onto a Schleicher and Schuell filter paper, No. 589, 11 cm in diameter through a Buchner funnel. The resultant composite film of collagen-mucopolysaccharide was removed from the filter paper and immersed in 0.02 M solution of glutaraldehyde and processed as in Example 4. The thickness of the resultant film was 15-17 mils.

The composite film was then blotted dry and a 5-mil coat of medical Grade Silastic silicone adhesive type A (Dow Corning Co.) was applied to the surface by knifing with a spatula. The coated composite was placed in a dessicator at 100% RH and 73° C for 16 hours. The resultant coated film was evaluated as a synthetic skin after sterilization in isopropyl alcohol and washing in sterile distilled water and sterile Dulbecco's solution.

EXAMPLE 14

In Vivo Grafting of Multilayer Synthetic Skin

Collagen-chondroitin 6-sulfate composites coated with silicone resin, prepared as in Example 13, were cut to the desired dimensions (4 cm × 6 cm) and immersed in 70/30 isopropanol/water for 24 hours at 23° C for disinfection. Handling of specimens was done in a sterile atmosphere supplied by a Tenney Relialab Laminar flow hood. Surgeon's gloves and masks were used during specimen handling. Following removal from the alcohol solution, the specimens were washed twice with sterile distilled water and then stored in Dulbecco's solution at 4° C until needed. At the end of this procedure, bacteriological testing of collagen-chondroitin 6-sulfate specimens for gram positive and gram negative bacteria and for anaerobics routinely gave negative results.

Grafting was carried out under aseptic conditions. White, Hartley, female guinea pigs, weighing approximately 400 grams, were used as subjects. For 7 days prior to grafting, a weight change history was recorded for each animal. Shortly before grafting the back of each animal was sheared with electric clippers over an area of 6 cm × 5 cm and loose hair clippings carefully removed with vacuum suction. The animal was then anesthesized by exposure to a mixture of oxygen and halothane and its back washed with 70/30 isopropanol/water.

Incisions covering an area of 4 cm × 6 cm were made according to an outline, made with iodine solution, which conformed to the size of the graft. The skin was excised over the panniculus carnosus, taking care to induce only minimal bleeding. Any blood in the wound was removed by patting with sterile gauze pads wet with sterile saline. The graft was placed over the wound bed in close juxtaposition to the skin at the perimeter of the wound. The graft was affixed by suturing with nylon suture, using approximately 16 sutures to close the wound. The animal was covered with a bandage encircling its body and secured around the neck to prevent slippage. Each animal under test was housed in a separate cage for the duration of the experiment.

The animals under test were weighed each day and the weight recorded. After 5 days the bandage was opened and the graft site examined. Animals were sacrificed at varying intervals and the graft and wound bed excised, and divided into two equal sections. One section was submitted for histological examination and the other examined without further treatment under a low-powered microscope. By lifting the graft material from the tissue with suitable tweezers, an examination of the condition of the wound site and the graft could be made. For periods up to at least 10 days, there was evidence of tissue undergrowth into the graft and no indication of wound contraction or acute inflammation.

Epitheliazation was minimal at the perimeter of the wound bed.

EXAMPLE 15

Collodion Coated Collagen-Chondroitin 6-Sulfate Multilayer Membrane

A collagen-chondroitin 6-sulfate composite prepared in accordance with Example 5 was grafted on a guinea pig in accordance with procedure in Example 14. After suturing, the entire graft and about ⅛ inch of neighboring skin was coated with a collodion solution (cellulose ester in suitable organic solvent) and allowed to dry thoroughly before application of bandage. The behavior of graft and tissue was similar to that of Example 14 except that by the 10th day the coating cracked due to embrittlement and dehydration of the collagen-chondroitin 6-sulfate occurred, with consequent contraction of the wound and epitheliazaton along the edges of the wound site.

Those skilled in the art will know, or be able to ascertain by no more than routine experimentation, many equivalents to the specific embodiments expressly described herein. These are within the scope of this invention and intended to be covered by the appended claims.

What is claimed is:

1. A multilayer membrane, comprising:
   a. a first layer formed from a crosslinked collagen-mucopolysaccharide composite containing at least about 0.5% by weight mucopolysaccharide; and,
   b. a moisture transmission control layer formed from a nontoxic material, said moisture transmission control layer providing said multilayer membrane with a moisture flux of from about 0.1 to about 1 mg/cm$^2$/hr.

2. A multilayer membrane of claim 1 wherein said moisture transmission control layer is formed form a natural polymer.

3. A multilayer membrane of claim 1 wherein said moisture transmission control layer is formed from a synthetic polymer.

4. A multilayer membrane of clam 3 wherein said collagen-mucopolysaccharide composite contains a sulfate-containing mucopolysaccharide.

5. A multilayer membrane of claim 4 wherein said collagen-mucopolysaccharide composite contains from about 6% to about 12% by weight of said sulfate-containing mucopolysaccharide.

6. A multilayer membrane of claim 5 wherein said sulfate-containing mucopolysaccharide is selected from chondroitin 6-sulfate, chondroitin 4-sulfate, heparin, heparan sulfate, keratan sulfate or dermatan sulfate.

7. A multilayer membrane of claim 6 wherein said collagen-mucopolysaccharide composite is crosslinked to an $M_c$ value of between about 800 and about 60,000.

8. A multilayer membrane of claim 7 wherein said sulfate-containing mucopolysaccharide is chondroitin 6-sulfate.

9. A multilayer membrane of claim 8 wherein said moisture transmission control layer is formed from a synthetic polymer selected from silicone resins, polyacrylate esters, polymethacrylate esters and polyurethanes.

10. A multilayer membrane of claim 4 wherein said moisture transmission control layer is formed from a synthetic polymer selected from silicone resins, polyacrylate esters, polymethacrylate esters and polyurethanes.

11. A multilayer membrane of claim 8 wherein said moisture transmission control layer is formed from a silicone resin.

12. A multilayer membrane of claim 11 wherein said moisture transmission control layer provides said multilayer membrane with a moisture flux of from about 0.3 to about 0.5 mg/cm$^2$/hr.

13. A multilayer membrane of claim 12 having an overall thickness of from about 25 to about 100 mils.

14. A multilayer membrane of claim 1 having an overall thickness of from about 25 to about 100 mils.

15. Synthetic skin comprising a first layer formed from a crosslinked collagen-mucopolysaccharide composite bonded to a nontoxic moisture transmission control layer which provides said synthetic skin with a moisture flux of from about 0.1 to about 1 mg/cm$^2$/hr.

16. Synthetic skin of claim 15 wherein said moisture transmission control layer is a synthetic polymer.

17. Synthetic skin of claim 16 wherein said synthetic polymer is selected from silicone resins, polyacrylate esters, polymethacrylate esters and polyurethanes.

18. Synthetic skin of claim 16 wherein said synthetic polymer is a silicone resin.

19. Synthetic skin of claim 18 wherein said collagen-mucopolysaccharide composite material contains from about 6% to about 12% of a sulfate-containing mucopolysaccharide and wherein said composite is crosslinked to an $M_c$ value of from about 5000 to about 10,000.

20. Synthetic skin of claim 19 wherein said sulfate-containing mucopolysaccharide is chondroitin 6-sulfate.

21. Synthetic skin of clam 20 having an overall thickness of from about 25 to about 100 mils.

22. Synthetic skin of claim 15 having an overall thickness of from about 25 to about 100 mils.

23. Synthetic skin comprising a multilayer membrane having a first layer formed from a crosslinked collagen-mucopolysaccharide composite and a moisture control layer which provides the multilayer membrane with a moisture flux substantially equal to normal skin.

24. A multilayer membrane, useful as synthetic skin, comprising:
   a. a first layer formed from a crosslinked collagen-mucopolysaccharide composite material which: (1) has controllable degradability in the presence of body enzymes; (2) has controllable solubility in the presence of body fluids; (3) is substantially nonimmunogenic upon grafting or implantation; and, (4) provokes no substantial foreign body response upon grafting or implantation; and,
   b. a moisture transmission control layer which provides the multilayer membrane with a moisture flux substantially equal to normal skin.

* * * * *